US006511677B1

(12) United States Patent
Brey et al.

(10) Patent No.: US 6,511,677 B1
(45) Date of Patent: *Jan. 28, 2003

(54) POLYMERIZABLE FATTY ACIDS, PHOSPHOLIPIDS AND POLYMERIZED LIPOSOMES THEREFROM

(75) Inventors: Robert N Brey, Alpharetta, GA (US); Likan Liang, Wheeling, IL (US)

(73) Assignee: Orasomol Technologies, Inc., Lake Bluff, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/714,103

(22) Filed: Nov. 17, 2000

Related U.S. Application Data

(63) Continuation of application No. 09/002,145, filed on Dec. 31, 1997, now Pat. No. 6,187,335.

(51) Int. Cl.$^7$ ............ A61K 9/127; C07C 69/34; C07C 230/00
(52) U.S. Cl. ............ 424/450; 560/198; 564/123; 514/557
(58) Field of Search ............ 424/450, 400, 424/1.21, 9.321, 9.51, 417, 94.3; 428/402.2; 935/54; 514/557; 560/198; 564/123

(56) References Cited

U.S. PATENT DOCUMENTS

| | | | |
|---|---|---|---|
| 4,248,829 A | 2/1981 | Kitajima et al. | 422/56 |
| 4,485,045 A | 11/1984 | Regen | 260/403 |
| 4,594,193 A | 6/1986 | Regen | 260/399 |
| 4,808,480 A | 2/1989 | Regen | 428/402.2 |
| 5,160,740 A | 11/1992 | Hasegawa et al. | 424/450 |
| 5,171,578 A | 12/1992 | Bally et al. | 424/450 |
| 5,204,096 A | 4/1993 | Neurath et al. | 424/89 |
| 5,258,499 A | 11/1993 | Konigsberg et al. | 530/351 |
| 5,366,881 A | 11/1994 | Singh et al. | 435/177 |
| 5,466,467 A | 11/1995 | Singh | 424/450 |
| 5,643,599 A | 7/1997 | Lee et al. | |

FOREIGN PATENT DOCUMENTS

WO 95/03035 2/1995

OTHER PUBLICATIONS

Allen et al., *Biochim. Biophys. Acta*, 1237, 99–108 (1995).
Amerongen et al., *J. Virology*, 68(12), 8428–8432 (1994).
Amaraki et al., *Pharmaceutical Research*, 1, 1228–1331 (1993).
Brey, *4th U.S.–Japan Symposium on Drug Delivery Systems* (1997).
Chen et al., *Proceed. Intern. Symp. Control. Rel. Bioact. Mater.*, 22, 204–205 (1995).
Chen et al., *Pharmaceutical Research*, 13(9), 1378–1383 (1996).
Chen et al., *3rd U.S.–Japan Symposium on Drug Delivery Systems* (1995).
Childers et al., *Regional Immunology*, 3, 8–16 (1990).
Clark et al., *Histochem. Cell Biol.*, 104, 161–168 (1995).
Comfurius et al., *Biochim. Biophys. Acta*, 488, 36–42 (1977).
Estrada et al., *Vaccine*, 13(10), 901–907 (1995).
Giannasca et al., *Am. J. Physiol.*, 267, G1108–1121 (1994).
Jones et al., *J. Experimental Medicine*, 180, 15–23 (1994).
Kirpotin et al., *Biochemistry*, 36, 66–75 (1997).
Parr, J. M. et al., *Biochim. Biophys. Acta* 1195, 21–30 (1994).
Regen, in *Liposomes: From Biophysics to Therapeutics*, (Ostro, ed.), Marcel Dekker, Inc., N.Y., pp. 73–108 (1987).
Sampaio et al., *J. Immunology*, 155, 2477–2486 (1995).
Shuhinian, S. et al, *Biochemistry* 34, 3813–3822 (1995).
Silvius, J. R. et al, *Biochemistry* 32, 3153–3161 (1993).
Silvius, J. R. et al, *Biochemistry* 32, 13318–13326 (1993).
Silvius, J. R. et al, *Biochemistry* 33, 3014–3022 (1993).
Singh et al., in *Phospholipids Handbook*, Gregor Cevc, pp. 233–291 (1993).
van Wijk, G.M.T. et al., *Biochemistry* 31, 5912–5917 (1992).
Zalipsky, S. et al, "Long circulating, cationic liposomes containing amino–PEG–phosphatidylethanolamine," FEBS Letters. 1994, vol. 353, pp. 71–74.
Zalipsky et al., *Bioconjugate Chem.*, 8(2), 111–118 (1997).

*Primary Examiner*—Gollamudi S. Kishore
(74) *Attorney, Agent, or Firm*—Pennie & Edmonds LLP

(57) ABSTRACT

The invention relates to an oral drug delivery system which delivers biologically active substances to the mucosal tissue of the intestine utilizing novel polymerized liposomes. Novel polymerizable fatty acids having a polymerizable group, a surfactant group, and a functional group, and optionally coupled to ligands which target mucosal tissue in the intestine are disclosed. Novel negatively charged polymerizable lipids which have phosphatidyl inositol (PI), phosphatidyl glycerol (PG) or phosphatidyl serine (PS) groups on a polymerizable backbone are also described.

5 Claims, No Drawings

POLYMERIZABLE FATTY ACIDS, PHOSPHOLIPIDS AND POLYMERIZED LIPOSOMES THEREFROM

This is a continuation of application Ser. No. 09/002,145, filed Dec. 31, 1997, now U.S. Pat. No. 6,187,335.

1. INTRODUCTION

The present invention relates to novel polymerizable fatty acids and phospholipids useful for preparing polymerizable liposomes for oral and/or mucosal delivery of vaccines, allergens, diagnostics and therapeutics. In particular, the present invention relates to polymerizable fatty acids having a polymerizable group, a surfactant group, and a functional group, such as octadecadienoyl-polyethylene glycol-succinic acid (ODPEGSu) compounds, and polymerizable liposomes prepared therefrom. The present invention further relates to polymerizable fatty acids coupled to targeting ligands with an affinity for human and mammalian intestinal M cells and similar cells in the nasopharyngeal cavity, such as lectins or proteins or peptides which can bind to M cells, and to polymerizable liposomes incorporating them. The invention also relates to negatively charged polymerizable lipids, specifically derivatives of polymerizable liposomes which have phosphatidyl inositol (PI), phosphatidyl glycerol (PG) or phosphatidyl serine (PS) groups on a polymerizable backbone, and to liposomes prepared therefrom. The invention still further relates to the use of the polymerized liposomes of the present invention as, or in, pharmaceutical compositions for oral delivery of a variety of diagnostic or therapeutic agents, including drugs, allergens and vaccines. The liposomes of the present invention provide increased stability in the gastrointestinal (G-I) tract, and increased flexibility in targeting liposomes to particular cells to enhance the uptake of encapsulated therapeutic agents.

2. BACKGROUND OF THE INVENTION

2.1. Drug Delivery

Drug delivery takes a variety of forms, depending on the agent to be delivered and the administration route. The most convenient way to administer drugs into the body is by oral administration. However, many drugs, in particular proteins and peptides, are poorly absorbed and unstable during passage through the gastrointestinal (G-I) tract. The administration of these drugs is generally performed through parenteral injection.

Although oral vaccination is more convenient, vaccines are generally given through injection. This is particularly true with killed or peptidic vaccines, because of their low absorbability and instability in the G-I tract. A problem with systemic immunization is that it may not effectively induce mucosal immune responses, particularly production of IgA, that are important as the first defense barrier to invaded microorganisms. For this reason, it would be beneficial to provide oral vaccination, if the problems of low absorbability and instability could be overcome.

Controlled release systems for drug delivery are often designed to administer drugs to specific areas of the body. In the gastrointestinal tract it is important that the drug not be eliminated before it has had a chance to exert a localized effect or to pass into the bloodstream.

Enteric coated formulations have been widely used for many years to protect drugs administered orally, as well as to delay release. Several microsphere formulations have been proposed as a means for oral drug delivery. For example, PCT/US90/06433 by Enzytech discloses the use of a hydrophobic protein, such as zein, to form microparticles; U.S. Pat. No. 4,976,968 to Steiner et al. discloses the use of "proteinoids" to form microparticles; and European Patent Application 0,333,523 by the UAB Research Foundation and Southern Research Institute discloses the use of synthetic polymers such as polylactic acid-glycolic acid to form microspheres.

Particles less than ten microns in diameter, such as the microparticles of EPA 0,333,523, can be taken up by cells in specialized areas, such as Peyer's patches and other intestinal mucosal lymphoid aggregates, located in the intestine, especially in the ileum, into the lymphatic circulation. Entrapping a drug or antigen in a microparticulate system can protect the drug or antigen from acidic and enzymatic degradation, yet still allow the drug or antigen to be administered orally, where they are taken up by the specialized uptake systems, and release the entrapped material in a sustained manner or are processed by phagocytic cells such as macrophages. When the entrapped material is a drug, elimination of the first-pass effect (metabolism by the liver) is highly advantageous.

2.2. Liposomes

Conventional liposomes have been proposed for use as an oral drug delivery system, for example, by Patel and Ryman, *FEBS Letters* 62(1), 60–63 (1976). Liposomes are typically less than 10 microns in diameter, and, if they were stable to passage through the G-I tract, may be absorbed through Peyer's patches (Aramaki, Y., H. Tomizawa, T. Hara, K. Yachi, H. Kikuchi, and S. Tsuchiya, 1993 Stability of liposomes in vitro and their uptake by rat Peyer's patches following oral administration. *Pharm. Res.* 10:1338, 1331; Childers, N., F. R. Donya, N. F. Magoo, and S. M. Michalek 1990. Ultrastructural study of liposome uptake by M cells of rat Peyer's patch: an oral vaccine system for delivery of purified antigen. *Regional Immunology* 3:8–16). Liposomes also have some features that should be advantageous for a particulate system for oral drug or antigen delivery. The phospholipid bilayer membrane of liposomes separates and protects entrapped materials in the inner aqueous core from the outside. Both water-soluble and -insoluble substances can be entrapped in different compartments, the aqueous core and bilayer membrane, respectively, of the same liposome. Chemical and physical interaction of these substances can be eliminated because the substances are in these different compartments. Further, liposomes are easy to prepare. However, liposomes are physically and chemically unstable, and rapidly leak entrapped material and degrade the vesicle structure. Without fortifying the liposomes, they are not good candidates for oral drug or antigen delivery. Thus, despite the early proposal for use of conventional liposomes in oral drug delivery, their use has still not been accepted.

Several methods have been tried to fortify liposomes. Some methods involve intercalating cholesterol into the bilayer membrane or generating the liposomes using phospholipids with high melting temperature or physically stabilizing preformed liposomes with excipients such as simple sugars or polysaccharides. Generally, these methods are not believed to be sufficient in making liposomes for oral delivery since during oral delivery liposomes are exposed to an acidic Ph in the stomach and bile salts and phospholipases in the intestine. These conditions typically dissolve the characteristic liposomal bilayer membrane and contents are released and degraded.

2.3. Polymerized Liposomes

Polymerization of liposomes has been shown in vitro to be an effective means of stabilizing the liposomes and reducing problems of degradation, agglomeration, and leakage of encapsulated drugs. Polymerized liposomes have been developed in attempts to improve oral delivery of encapsulated drugs (Chen et al., WO 9503035). The ability of polymerized liposomes to survive the G-I tract has also been investigated (Chen et al., 1995, *Proceed. Internat. Symp. Control. Rel. Bioact. Mater.* 22; Chen et al., 1995 Proc. 3rd U.S. Japan Symposium on Drug Delivery Systems; Brey, R. N., 1997, Proc. 4th U.S. Japan Symposium on Drug Delivery).

A number of compounds have been reported to form polymerized liposomes. For example, U.S. Pat. No. 4,248,829 discloses phospholipids containing di-yne acyl chains polymerizable by ultraviolet light to yield intermolecular or intramolecular cross-linking.

U.S. Pat. No. 4,485,045 discloses polymerizable phosphatidyl choline derivatives containing an unsaturated lower aliphatic acyloxy longer chain alkanoyloxy moiety. The polymerizable site in the phosphatidyl choline derivatives is a terminal ethylene group on the acyloxy substituent.

U.S. Pat. No. 4,808,480 discloses heterocyclic compounds containing disulfide bonds that are used to form polymerizable phospholipids. The phospholipids incorporate the heterocyclic disulfide compounds as terminal substituents on the glyceryl acyl groups, and polymerize upon ring-opening of the heterocyclic substituents.

U.S. Pat. No. 4,594,193 discloses polymerizable lipid compounds containing mercaptan groups. These lipids polymerize by formation of intermolecular disulfide linkages.

U.S. Pat. No. 5,160,740 discloses polymerization of a polymerizable 2,4-diene phospholipid, cholesterol, and a polymerizable 2,4-diene fatty acid to form a polymerized macromolecular endoplasmic reticulum. The reticulum is reported to be stable in surfactant solutions and capable of enclosing hemoglobin.

U.S. Pat. No. 5,466,467 discloses derivatives of phosphatidyl choline containing polymerizable acyl chain moieties and metal-chelating groups. The phospholipids contain iminodiacetic acid covalently bonded to the choline in the polar head group. Cross linked phospholipid membranes generated from monomeric units can be used to immobilize enzymes and proteins on the surface of the liposomes via metal bridges.

Further, U.S. Pat. No. 5,366,881 discloses phosphatidyl choline derivatives containing different polymerizable groups positioned at various sites in the acyl chains to achieve altered membrane fluidity properties. Additionally, the mixture of non-polymerizable phospholipids with polymerizable phospholipids provides for bilayer liposomes capable of conditional release of encapsulated material.

A number of additional polymerizable phospholipids are described in Regen, in Liposomes: from Biophysics to Therapeutics (Ostro, ed., 1987), Marcel Dekker, N.Y. Additional polymerizable moieties contained within the acyl chains of phospholipids or within the polar head group have been described and are found in Singh, A., and J. M. Schnur, 1993, "Polymerizable Phospholipids", in Phospholipids Handbook, Gregor Cevc, ed., Maroel Dekker, New York. Various other polymerizable phospholipids and fatty acids have been described, having methacrylate, vinylbenzene, diacetylenes, and azidoformaloxy groups within the structure of the acyl chains.

Although polymerized liposomes, generally, are more stable than their unpolymerized counterparts, it is not clear that the improved stability thus far achieved is by itself sufficient to enable these liposomes to deliver effective doses of drugs administered orally. Recent studies have investigated the possibility of modifying polymerized liposomes to contain a molecule or ligand which selectively targets M cells and other absorptive cells in the mammalian intestine (Chen et al., 1996, *Pharmaceutical Research* 13:1378–1383). Incorporation of a targeting ligand is believed to increase the adhesion efficiency of the modified polymerized liposome on M cell surfaces, and thus to increase the efficiency of absorption of drugs encapsulated in those liposomes. M cells are specialized epithelial cells dispersed within the follicle associated epithelium (FAE) overlying the Peyer's patches in mammalian small intestine. The use of targeting ligands specific for surface receptors on M cells, enterocytes or other cells requires new chemistries to effectively incorporate such ligands without compromising the stability or safety of the polymerized liposome.

A variety of methods have been described for covalently coupling of bioactive ligands to the surface of conventional liposomes. U.S. Pat. No. 5,171,578 discloses the chemical coupling of the glycoprotein streptavidin to the surface of liposomes via a modified phosphatidyl ethanolamine. Because of selective binding affinity to biotin, such surface modified liposomes can be used to directly bind biotinylated proteins to their surface.

U.S. Pat. No. 5,204,096 describes the covalent coupling of peptides to the surface of liposomes by activating peptides with carbodiimide followed by coupling to active carboxyl groups exposed on the surface of liposomes. In this case, surface carboxyl groups are provided by the inclusion of aminoalkanes, such as stearylamine or diamino alkanes in the lipid bilayer.

U.S. Pat. No. 5,258,499 discloses the preparation of a liposome cytokine complex in which the procedure for covalent attachment of receptor-binding interleukin-2 involves treatment of the cytokine with succinimidyl-4-(p-maleimidophenyl)butyrate as a linker followed by linkage to activated liposome surfaces. In this case, the activated liposome surface consists of phosphatidyl ethanolamine modified with succinimidyl-S-acetylthioacetate.

Zalipsky et al (Zalipsky, S., Mullah, N., Harding, J. A., Gittelman, J., Guo, L. and DeFrees, S. A., 1997, *Bioconjug. Chem.* 8:111–118) described the synthesis of a lipid anchor for the surface modification of liposomes, containing distearoylphosphatidylethanolamine (DSPE) as a lipid anchor, heterobifunctional polyethylene glycol (PEG) with a molecular weight of 2000 as a linking moiety, and biological cell adhesive ligand [YIGSR peptide or Sialyl Lewis (X) oligosaccharide (SLX)]. Allen et al (Allen, T. M., Brandeis, E., Hansen, C. B. Kao, G. Y. Zalipsky, S. 1995. *Biochim Biophys Acta.* 1237:99–108) described the derivitization of the surface of sterically stabilized liposomes. The polyethylene glycol (PEG)-lipid derivative pyridylthiopropionoylamino-PEG-distearoylphosphatidylethanolamine (PDP-PEG-DSPE) was synthesized and incorporated into liposomes. Thiolysis of the PDP groups resulted in formation of reactive thiol groups on the liposome surface which reacted with maleimide-activated antibodies to yield covalent attachment of the antibodies. Kirpotin et al (Kirpotin, D., Park, J. M., Hong, K., Zalipsky, S., Li, W. L., Carter, P., Benz, C. C., Papahadjopoulos, D. 1997. *Biochemistry* 36:66–75) described the formation of liposomes conjugated via PEG-modified distearoylphosphatidyl phosphatidylethanolamine to Fab fragments of a humanized recombinant Mab against the extracellular domain of the breast cancer marker HER2/neu by maleimide-terminated membrane-anchored spacers of two kinds for covalent attachment at the distal terminus of the PEG chain.

2.4. Lectin Targeting of Liposomes

Lectins have been proposed as promising moieties to use as targeting ligands. Lectins are a broad group of proteins, usually glycoproteins of plant origin, with binding specificity for particular carbohydrates. Like any targeting ligand, lectins can be covalently bound to the lipids of the liposome, or can be non-covalently attached to the liposome by a combination of short-range intermolecular forces and simple steric entanglement. Surface-bound lectins can aid in the selective targeting of liposomes with entrapped drug or antigen to carbohydrate counter-ligands expressed on cell receptors or other surface glycoproteins. In order to effectively target particular cells, the lectins must be attached to the liposome so that the site-specific portion of the lectin is exposed and available for binding to cells. Additionally, the targeting lectin must be incorporated into the liposome in a manner that does not destabilize the liposome or allow physical release of the targeting ligand from the liposome surface. A wide variety of lectins with selectivity to intestinal absorptive cells and M cells has been identified (Gianasca, P. J., K. T. Gianasca, P. Falk, J. I. Gordon, and M. R. Neutra 1994. *Gastrointen. Liver Physiol.* 30:G1108–1121; Clark, M. A., M. A. Jepson, and B. H. Hirst 1995. Lectin binding defines and differentiates M-cells in mouse small intestine and caecum. *Histochem Cell Biol.* 104:161–168). Recent work has shown that lectins with selectivity to intestinal M cells and enterocytes can be incorporated into liposome bilayers and the liposomes subsequently polymerized (Chen et al., 1996, *Pharmaceutical Research* 13:1378–83). These lectin-modified polymerized liposomes show increased efficacy in targeting liposomes to Peyer's patches in the G-I tract. However, the lectin-modified anchoring lipids used in these studies were not structurally optimized for stability within the polymerized liposome bilayer and formed patches of non-polymerized lipids that contributed to instability.

Despite the advances in liposome technology and drug delivery, there remains a need for stable and efficacious polymerized liposomes, and new polymerizable compounds that can be incorporated into polymerizable liposomes to improve stability, binding selectivity, and efficiency of drug delivery. There additionally remains a need for new processes to manufacture polymerizable liposomes incorporating targeting molecules or ligands, and to manufacture polymerizable liposomes which encapsulate drugs.

3. SUMMARY OF THE INVENTION

The present invention encompasses novel chemical compounds useful for the preparation of polymerizable liposomes, and polymerizable liposomes made therefrom. The novel chemical compounds can be used to create polymerizable liposomes with improved properties, including enhanced stability in the G-I tract, increased ability to target specific cells, and ability to effectively deliver therapeutics and diagnostics and other agents orally or mucosally. The invention is particularly suited for the delivery of oral vaccines.

The present invention encompasses, in one embodiment, novel polymerizable fatty acids comprising a polymerizable group such as 2,4 octadecadienoyl (2,4OD), a surfactant group such as polyethylene glycol (PEG), and an acid functional group such as succinic acid (Su) and chemically stable linkages between the groups. The polymerizable group can contain a variety of polymerizable moieties such as double bonds, triple bonds, or thiol groups. In a particularly preferred embodiment, the polymerizable fatty acids have the formula:

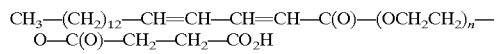

$CH_3-(CH_2)_{12}-CH=CH-CH=CH-C(O)-(OCH_2CH_2)_n-O-C(O)-CH_2-CH_2-CO_2H$ where n is an average number of monomer units, determined by the average molecular weight of the polyethylene reagent used. The molecular weight ranges from about 200 to about 2000 g/mol.

The present invention also relates to polymerizable fatty acids which have been coupled to a ligand, such as a lectin, or molecule capable of targeting intestinal M-cells and absorptive enterocytes and similar cells lining the nasopharyngeal cavity.

The present invention also relates to polymerized liposomes which incorporate the polymerizable fatty acids, either as coupled to a targeting ligand such as a lectin, or in a non-derivatized form. These polymerized liposomes are is obtained, inter alia, by polymerizing a mixture of a polymerizable lipid and a polymerizable fatty acid or a polymerizable fatty acid coupled to a targeting ligand, and optionally other non-polymerizable phospholipids and/or cholesterol.

The present invention also relates to polymerizable lipids which contain a negatively-charged hydrophilic group, such as phosphatidyl inositol (PI), phosphatidyl glycerol (PG) or phosphatidyl serine (PS). These polymerizable lipids can be based on a glyceryl backbone such as 1,2-di(2,4-octadecadienoyl) or other polymerizable lipid backbone.

3.1. Definitions

As used herein, the term "liposome" is defined as an aqueous compartment enclosed by a lipid bilayer. (Stryer, *Biochemistry, 2d Edition*, W.H. Freeman & Co., p. 213 (1981)). The liposomes can be prepared by a thin film hydration technique followed by a few freeze-thaw cycles which are known in the art. Liposomal suspensions can also be prepared according to methods known to those skilled in the art, for example, as described in U.S. Pat. No. 4,522,811, which is incorporated herein by reference in its entirety.

As used herein, the term "polymerized liposome" is defined as a liposome in which some, most or all of the constituent phospholipids are covalently bonded to each other by inter and/or intra molecular interactions. The phospholipids can be bound together within a single layer of the phospholipid bilayer (the leaflets) and/or bound together between the two layers of the bilayer.

As used herein, the term "conventional liposome" refers to an unpolymerized liposome.

The degree of polymerization in the polymerized liposomes can range from 30 to 100 percent; i.e., up to 100 percent of the available bonds are formed. The size range of polymerized liposomes is between approximately 15 nm to 10 μm. The polymerized liposomes can be loaded with up to 100% of the material to be delivered, when the material is hydrophobic and attracted by the phospholipid layers. In general, about 5 to about 40 percent of the material is encapsulated when the material is hydrophilic.

As used herein, the term "trap ratio" is defined as the ratio of inner aqueous phase volume to total aqueous phase volume used.

As used herein, the term "radical initiator" is defined as a chemical which initiates free-radical polymerization.

As used herein, the term "reverse phase evaporation technique" is defined as a method involving dissolving a lipid in an organic solvent, adding a buffer solution, and evaporating the organic solvent at reduced pressure, as described by Szoka, F. Jr., and Papahadjopoulos, D., *Proc. Natl. Acad. Sci. USA*, Volume 75, No. 9, pp. 4194–4198 (1978).

As used herein, the term "freeze-thaw technique," or "F-T," is defined as freezing a suspension in a cryogenic fluid such as liquid nitrogen, and subsequently thawing the suspension in a roughly 30° C. water bath.

As used herein, the terms "mucosa" or "mucosal tissue" refers to a epithelial tissue, such as intestinal lamina propria, a layer of smooth muscle in the digestive tract, nasopharyngeal epithelial tissue, lung epithelial tissue, ocular epithelial tissue, or vaginal epithelial tissue. Usually, these tissues are protected by a layer of mucous, a complex mixture of mucin and other proteins up to 200 µm thick, which serves as a mechanical barrier against microbial pathogens and as a milieu for secreted effectors such as secretory immunoglobulins. Mucosal delivery as used herein is meant to include delivery through bronchi, gingival, lingual, buccal, nasal, oral, vaginal and intestinal mucosal tissue.

As used herein, the term "buffer solution" is defined as an aqueous solution or aqueous solution containing less than 25% of a miscible organic solvent, in which a buffer has been added to control the Ph of the solution. Examples of suitable buffers include but are not limited to PBS (phosphate buffered saline), TRIS (tris-(hydroxymethyl) aminomethane), HEPES (hydroxyethylpiperidine ethane sulfonic acid), and TES (2-[(tris-hydroxymethyl)methyl] amino-1-ethanesulfonic acid).

As used herein, the term "leaflets" is defined as a single layer of phospholipids in the bilayer forming the liposome.

4. DETAILED DESCRIPTION OF THE INVENTION

The invention relates to an oral or mucosal drug delivery system to deliver drugs to the mucosal tissue of the intestine and other epithelial surfaces which utilizes polymerized liposomes as the drug carriers. More specifically, the invention relates to novel polymerizable fatty acids, novel polymerizable phospholipids and liposomes made therefrom. The polymerizable fatty acids and phospholipids are used to prepare liposomes with significant stability in the G-I tract. Further, the polymerizable fatty acids and phospholipids can be used to covalently attach targeting molecules to the liposomes, such as lectins which target M cells in intestinal Peyer's patches, absorptive intestinal enterocytes and other similar cells in other mucosal surfaces. The polymerizable fatty acids are used to improve the preparation and loading of the polymerized liposomes. The polymerized liposomes prepared using these novel fatty acids or phospholipids are especially useful for targeting the delivery of vaccines and antigens to M cells. The following describes the novel fatty acids and phospholipids, how they are prepared and how they can be utilized to prepare stable polymerized liposomes.

4.1. Polymerizable Fatty Acids

The present invention encompasses, in one embodiment, novel polymerizable fatty acids which can be used both to increase the stability of polymerized liposomes incorporating them, and to provide a functional acid linking group to conveniently, efficiently and effectively attach targeting ligands to polymerized liposomes. The polymerizable fatty acids comprise at one end a polymerizable group, at the other end an acid functional group, and a surfactant group, between the polymerizable and functional groups, forming the central portion of the fatty acid, and optionally chemically stable linking moieties between these groups. It is preferred that the functional group be an acid functional group.

For example, the structure of these novel fatty acids in one embodiment is:

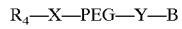

wherein $R_4$, the polymerizable group, is a lipophilic chain (fatty acid chain) with at least one polymerizable functional group that will enable polymerization; X or Y are independently a functional linkage such as an ester bond, an ether bond, an amide bond or a carbamate; B is an acid functionality, $-NH_2$, or an aldehyde; and PEG is the preferred surfactant group which can vary in molecular weight as described below.

The structure of these novel fatty acids gives them unique functionality and particular utility when used in conjunction with polymerizable liposomes. The polymerizable group allows the novel fatty acid molecules to co-polymerize with polymerizable phospholipids in a polymerizable liposome, so that the molecules are covalently bound to the polymerized liposome, rather than attached in a less-stable fashion, such as by intercalation or steric entanglement. The functional acid group provides a convenient reaction site which can be derivatized using known techniques to attach any targeting ligand capable of bonding to the acid or derivatized acid moiety. The surfactant group is disposed between the polymerizable group and the functional acid group, and comprises a polymeric chain with hydrophilic and hydrophobic regions.

The surfactant group serves several functional purposes. The length of the polymeric chain of the surfactant group can be chosen to be short or long, and the relative hydrophilicity/hydrophobicity of the chain can be altered, depending on the desired properties of the liposome. The polymeric chain should not be long enough to affect the ability of the lipophilic moiety to participate in the lipid packing. A long-chain surfactant group with significant hydrophilicity, for example, can extend away from the liposome into the surrounding solution, providing the liposome with numerous hydrophilic "hairs" protecting the liposome body and effectively "disguising" it to aid its passage through the G-I tract. A short-chain surfactant group with less hydrophilicity will stay closer to the body of the liposome, and will tend to coil and tangle, to give the liposome numerous hydrophilic coils or tangles close to the liposome surface. It will be appreciated that several configurations can be achieved, by varying the length and hydrophilicity of the polymer chain. When the fatty acid is coupled to a targeting ligand and incorporated into a polymerized liposome, the polymer chain of the surfactant group additionally serves as a "spacer" between the liposome and the targeting group, allowing the targeting group to be held closer or farther from the body of the liposome, as desired.

The polymerizable group can be any group capable of coupling to the surfactant group and co-polymerizing with polymerizable phospholipids. A wide variety of polymerizable groups are suitable, and it will be appreciated that the particular choice of polymerizable groups will depend upon the polymerizable phospholipid and surfactant groups chosen. For example, it is convenient to use a mono-, di- or polyunsaturated aliphatic carboxylic acid, which can polymerize with a polymerizable phospholipid through the double or triple bond or bonds, and can couple to hydroxy-terminated surfactant groups through the acid moiety. Specific examples of polymerizable groups include, but are not limited to, unsaturated aliphatic acid groups such as $CH_3(CH_2)_mCH=CH-CH=CHCOOH$ where the number of methylene groups (m) can vary from 4 to 12. The double bonds or polymerizable functionalities can be anywhere in the chain so long as they provide an environment suitable for polymerization and packing. One or more of such functionalities can be present in a molecule.

The surfactant group comprises a polymeric chain with hydrophilic and hydrophobic regions, capable of coupling to both the polymerizable group and the functional acid group. Polyethers such as polyethylene glycol, polypropylene glycol, and their copolymers, for example, are suitable surfactant groups. Poly(lactic acid) may also be used. A preferred surfactant group is polyethylene glycol, as it is readily coupled to the preferred enoic polymerizable groups and the preferred dioic functional acid groups discussed below.

The functional group can be an acid capable of coupling to the surfactant group. Diacids are preferred, as they are easily attached to the preferred polyether surfactant groups. Particularly preferred are saturated, aliphatic diacids of the formula:

HO—C(O)—(CH$_2$)$_b$—C(O)—OH where b is an integer from 0 (i.e., oxalic acid) to 12, preferably 0 to 4. Unsaturated diacids having from 2 to 14 carbon atoms are also suitable. For convenient coupling to the surfactant group, diacids which can be used in their anhydride form are especially preferred, such as succinic acid (succinic anhydride). Alternatively, the functional group can be an amine, an amide or diamine.

In a preferred embodiment, the polymerizable group is a 2,4-dienoyl, the surfactant is a polyethylene glycol group (PEG), and the functional group is a short-chain diacid acid group. In this embodiment, the fatty acids have the formula:

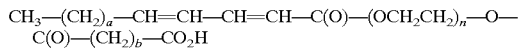

CH$_3$—(CH$_2$)$_a$—CH=CH—CH=CH—C(O)—(OCH$_2$CH$_2$)$_n$—O—C(O)—(CH$_2$)$_b$—CO$_2$H where a is an integer from 0 to 18, preferably 4 to 12, b is an integer from 0 to 12, preferably 0 to 4 and the value of n depends on the average molecular weight of the polyethylene glycol reagent used to synthesize the fatty acids; n can range from about 4 (PEG-200) to about 45 (PEG-2000). It will be appreciated that n is an average value, not generally integral, which characterizes a mixture of chain lengths present in commercially available polyethylene glycols of a particular molecular weight average.

In a more preferred embodiment, the polymerizable group is an 2,4 octadecadienoyl group (2,4OD), the surfactant is a polyethylene glycol group (PEG), and the functional acid group is a succinic acid group (Su). In this particularly preferred embodiment, the fatty acids have the formula

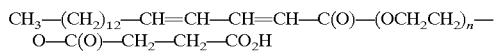

CH$_3$—(CH$_2$)$_{12}$—CH=CH—CH=CH—C(O)—(OCH$_2$CH$_2$)$_n$—O—C(O)—CH$_2$—CH$_2$—CO$_2$H where n is about 8.7, corresponding to the average n in PEG-400. A polyethylene glycol of any desired molecular weight can be incorporated into the 2,4-ODPEGSu fatty acid. For use with the targeting ligands described below, however, polyethylene glycols with average molecular weights from about 200 to about 2000 are preferred, and a molecular weight average of about 400 or about 1900 is most preferred. These preferred ODPEGSu polymerizable fatty acids can be formed by first reacting 2,4-octadecadienoic acid with a desired molecular weight polyethylene glycol to form 2,4-ODPEG, then derivatizing the ODPEG product with succinic anhydride to form ODPEGSu. For a detailed synthesis, see the Examples infra.

4.2. Targeted Polymerizable Fatty Acids

The novel polymerizable fatty acids of the present invention are easily derivatized and covalently linked to ligands capable of targeting particular cells in the G-I tract. The fatty acids are first coupled to a targeting ligand, then copolymerized with a polymerizable liposome, to form a stable, polymerized liposome with the desired targeting ligand covalently attached. The polymerization can be carried out in the presence of a desired therapeutic agent, such as a vaccine or antigen, or the polymerized liposome can be loaded with a therapeutic agent after polymerization, using known techniques. The resulting stable, targeted liposome can be used to effectively and selectively deliver therapeutic agents to M cells in the G-I tract. The targeted fatty acids of the present invention are thus especially useful for the oral delivery of therapeutic agents, such as vaccines.

The present invention encompasses the novel fatty acids described above, which have been further derivatized (if necessary) and coupled to a ligand or molecule capable of targeting particular cells in the gastrointestinal tract. It is expected that liposomes prepared with these targeted ligands will selectively bind to the targeted cells, thereby increasing the effectiveness of delivery of encapsulated drugs. The targeting ligand can be, for example, a lectin with an affinity for human and mammalian intestinal M cells. Preferred ligands are lectins such as EEA (Euonymus Europaeus), a fluorescently labelled EEA, FITC-EEA (fluorescein isothiocyante-EEA), UEA-I (Ulex Europaeus Agglutinin I), and WGA (Wheat Germ Agglutinin). Many other ligands are potentially useful for mucosal application; for example, class II framework Mab, (Estrada, A., M. R. McDermott, B. J. Underdown, and D. P. Snider. 1995. Intestinal immunization of mice with antigen conjugated to anti-MHC class II antibodies. *Vaccine*. 13:901–907), ICAM-1, or any protein or peptide ligand that selective binds to M cells including alkaline phosphatase, bacterial surface proteins (Jones, B. D., N. Ghouri, and S. Falkow. 1994. *Salmonella typhimurium* initiates murine infection by penetrating and destroying the specialized epithelial M cells of the Peyer's patches. *J. Exp. Med.* 180:15–23) or viral proteins (Amerongen, H., G. A. R. Wilson, B. N. Fields, and M. R. Neutra. 1994. Proteolytic processing of reovirus is required for adherence of intestinal M cells. *J. Virol.* 68:8428–8432) or ligands or antibodies having affinity for mucosal addressin cell adhesion molecule-1 (Madcam-1) (Sampaio, S. O., X. Li, M. Takeuchi, C. Mei, U. Francke, E. C. Butcher, and M. J. Briskin, 1995. Organization, regulatory sequences, and alternatively spliced transcripts of the mucosal addressin cell adhesion molecule-1 *J. Immunol.* 155:2477–2486).

In a preferred embodiment, the targeting ligand is a lectin such as EEA, and the fatty acid is a dienoyl-polyethylene glycol-diacid derivative, such as ODPEGSu. The coupling reaction to covalently attach a lectin to a fatty acid such as ODPEGSu can be carried out using the techniques known in the art such as that described in Chen et al., 1996, *Pharmaceutical Research* 13:1378–1383. The coupling of 2,4-ODPEGSu with EEA is shown in the Examples, infra.

The amount of targeting ligand used in the polymerizable liposome will depend on the specific target. In general, the ratio of targeting ligand to polymerizable material is about 10–100 molecules per liposomes (about 1/10,000 to about 1/1000 w/w).

4.3. Polymerized Liposomes Using Polymerizable Fatty Acids

The novel polymerizable fatty acids of the present invention can be used to form an oral drug delivery system to deliver drugs to the mucosal tissue of the intestine. The present invention thus encompasses polymerized liposomes which incorporate these novel polymerizable fatty acids, and the use of the polymerized liposomes as drug carriers. The fatty acids can be used either in their non-derivatized form, to enhance the stability of the polymerized liposomes, or coupled to a ligand which targets particular cells in the G-I tract, as described above. The polymerized liposomes are obtained by polymerizing a mixture of a polymerizable lipid and a polymerizable fatty acid or polymerizable polymer-coupled fatty acid or polymerizable targeted fatty acid of the present invention, using conventional liposome polymerization techniques, such as irradiation, redox initiation, radical initiation, and the like.

The polymerizable lipids used in conjunction with the polymerizable fatty acids and targeted polymerizable fatty acids of the present invention are not limited to any particular lipids. Any lipid can be used which is polymerizable and is capable of forming polymerized liposomes. A wide variety of polymerizable lipids have been described in the literature; see, e.g., Regen, in Liposomes: From Biophysics to Therapeutics (Ostro, ed., 1987), Marcel Dekker, N.Y., and Singh and Schnur, Polymerizable Phospholipids, in Phospholipids Handbook, 1993, Marcel Dekker, New York which are incorporated herein by reference. Preferred polymerizable lipids include diene containing phospholipids with uncharged head groups, such as glycerol, inositol, or serine, or charged head groups such as choline or ethanolamine. A particularly preferred polymerizable lipid is 1,2-di(2,4-octadecadienoyl)-3-phosphatidylcholine (DODPC).

The polymerizable fatty acids and targeted polymerized fatty acids can be any of the species described herein. Without being bound by any particular theory, it is believed that the 2,4-ODPEGSu fatty acid co-polymerizes with the polymerizable lipid, and that the hydrophilic tail of 2,4-ODPEGSu incorporated into the liposome extends away from the liposome surface and into any surrounding aqueous phase. The PEG chain thus enhances the stability of the liposome by creating a sterically stabilized liposome, in which the liposome body is somewhat protected by the protruding and entangled copolymerized ODPEGSu chains. Higher molecular weight polyethylene glycols (i.e., average molecular weight above about 2000) may destabilize the liposome, while lower molecular weight PEGs (i.e., average molecular weights from about 200 to 2000) will have a net stabilizing effect. The resulting polymerized liposomes thus have increased stability in the G-I tract and ability to pass through mucus layer, and additionally can be targeted to particular cells of the intestine when targeted polymerizable fatty acids are used.

When targeted fatty acids are used, the polymer chain of the surfactant group additionally serves as a spacer between the liposome and the targeting ligand attached to the fatty acid. Accordingly, the molecular weight of the polyethylene glycol should be chosen in order to achieve the desired spacing, while still allowing the fatty acid to copolymerize with the lipids. The lower molecular weight polyethylene glycols are thus believed to be more suitable; i.e., those with average molecular weights of about 200 to about 2000, preferably about 200 to about 1500, and most preferably about 400.

The polymerized liposomes of the present invention can additionally contain non-polymerizable compounds, so long as the amounts of polymerizable lipids and polymerizable fatty acids or targeted polymerizable fatty acids are sufficient to give the resulting polymerized liposomes adequate stability. For example, non-polymerizable fatty acids or non-polymerizable phospholipids known in the art and used for conventional liposome formation may be used. In addition, cholesterol can be used for added stability. A preferred non-polymerizable compound is cholesterol which can be included in molar ratios of up to 50% with the polymerizable components.

The polymerized liposomes of the present invention may be utilized for the delivery of a wide variety of compounds, including vaccines, antigens, allergens and other therapeutic agents or diagnostics. They have particular utility in the oral and/or mucosal delivery of vaccines and antigen release devices. For example, the polymerized liposomes of the present invention may be designed to carry a wide variety of antigens including, but not limited to, diphtheria toxoid, influenza hemeagglutinin, ospA antigen from Lyme disease bacterium, and HTLV envelope protein antigen. Antigens to poliovirus, rhinovirus, rabies, vaccinia, Epstein-Barr virus, hepatitis, HTLV, herpes virus and human immunodeficiency virus are just examples of the many types of antigens which may be encapsulated into the liposomes of the present invention. They may also be utilized for the oral delivery of a wide variety of therapeutics, including but not limited to, chemotherapy agents, antibiotics, insulin, cytokines, interferon, hormones, calcitonin, hormones, fertility drugs, antiviral agents (ddI, AZT, ddC, acyclovir and the like), antibacterial agents, antifungal agents, DNA and RNA nucleotides.

4.4. Negatively Charged Polymerizable Lipids

For still greater flexibility and utility in creating oral drug delivery systems, the present invention also encompasses novel polymerizable phospholipids with negatively charged groups. Incorporating negatively charged groups into a polymerized liposome greatly expands the use of the liposomes by taking advantage of the desirable properties of liposomes while additionally utilizing the electrostatic charge to improve and enhance the ability of the liposomes to entrap therapeutic agents. The resulting negatively charged polymerizable liposomes have superior trap ratios, and thus are especially effective in delivering the entrapped therapeutic agents.

The negatively charged polymerizable lipids of the present invention include polymerizable lipids which have phosphatidyl inositol (PI), phosphatidyl glycerol (PG) or phosphatidyl serine (PS) groups on a polymerizable backbone. These polymerizable lipids can be used to create polymerizable liposomes incorporating the negatively-charged PI, PG or PS groups, using conventional techniques. Because of capacity to interact with divalent cations, such negatively charged polymerizable phospholipids can assume alternate configurations in aqueous suspensions. In the presence of metal ions, for example, $Ca^{2+}$ or $Mg^{2+}$ ions, jelly-roll or cochelate structures can be formed; these structures consist of tightly packed bilayer membranes in which water has been squeezed out of the internal spaces. By harvesting such structures by centrifugation, followed optionally by lyophilization, and exposure to divalent metal-ion chelating agents, such as EGTA or EDTA, in the presence of drug or protein to be encaptured, a high and reproducible degree of loading of typically configured spherical bilayer liposomes can be obtained.

The negatively charged polymerizable lipids have the structure:

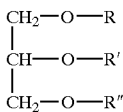

wherein at least one of R, R' or R" is independently phosphoryl inositol, phosphoryl glycerol or phosphoryl serine and at least one of the remaining two groups is a polymerizable group, consisting of acyl chains containing dienoic acids, diacetylenic acids, methacrylate side groups, acrylates, or thiol or disulfide containing acids. For example, the negatively charged polymerizable lipids may also have the following structure:

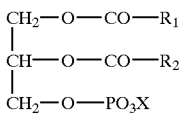

where X is glycerol, inositol or serine; and $R_1$ and $R_2$ are independently a polymerizable group selected from the group consisting of a diene group, a diacetylene group, a methacrylate group, and a thiol group. The polymerizable group is preferably a hydrocarbon chain containing one or more of the above-mentioned polymerizable moieties. The hydrocarbon chain can be from $C_4$ to $C_{30}$ and higher if desired. Although any polymerizable backbone can be used with these negatively charged polymerizable lipids, a particularly preferred backbone is 2,4-DODPC. Thus, a preferred negatively charged polymerizable lipid is

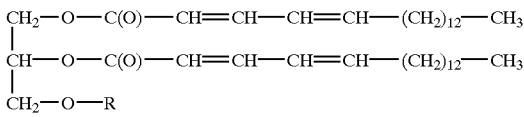

in which R is phosphoryl inositol, phosphoryl glycerol phosphoryl or serine.

These novel negatively charged polymerizable lipids can be synthesized according to the methods described in Confurius and Zwaal, *Biochimin Biophysica Acta*, 488:36–42 (1977) wherein polymerizable PG, PI or PS may be synthesized by a transphosphatidylation catalyzed by phospholipase D in the presence of protected glycerol, inositol or serine followed by a deprotection step. For example, DODPC is dissolved in diethyl ether (distilled from $P_2O_5$ to remove trace of alcohol) at a concentration of 20 mg/ml. L-serine is first lyophilized from a 10% (w/v) aqueous solution to remove trace of methanol and is subsequently dissolved at 45° C. at different concentrations up to saturation (46% w/v) in 100 mM acetate buffer (Ph 5.6) containing 100 mM $CaCl_2$. Phospholipase D is added to the serine solution at 45° C. to a final concentration of 1 IU/ml. An equal volume of the DODPC solution in ether is added and the incubation flask is immediately closed, in order to avoid ether evaporation. Incubation is carried out at 45° C. with stirring to complete mixing of both phases. Usually, two additional portions of phospholipase D equal to the starting amount are added after 30 minutes and 60 minutes respectively. Incubation is stopped after 90 minutes by addition of 100 mM EDTA (equivalent to two volumes of acetate buffer). Ether is evaporated at room temperature under a stream of nitrogen gas and the aqueous layer is mixed with 4.3 vol. of chloroform/methanol (5.8 v/v) and is stirred for 30 min. The single phase mixture is filtered through a glass filter G-2 and the filtrate is stirred for 10 min. with 1 volume of water and 3.7 volumes of chloroform. After centrifugation (10 min, 3000×g) the lower chloroform layer is collected and mixed with an equal volume of absolute ethanol, followed by evaporation to dryness under reduced pressure. The residue is dissolved in chloroform. Similar incubation is carried out at 37° C. in which serine is replaced by ethanolamine, glycerol, methanol, or ethanol in order to establish optimal conditions leading to the highest yields of DODPS.

The negatively charged polymerizable phospholipids, chelated with metal ions such as $Ca^{2+}$, can be formed into water-free liposomes and converted into spherical bilayer liposomes by exposure to chelating agents. Additionally, negatively charged polymerizable phospholipids can be mixed with the novel fatty acids and targeted fatty acids described above, and water-free composite structures can be formed in the presence of divalent cations. Following conversion of water-free liposomes to spherical liposomes with internal aqueous space in the presence of chelating agents, resulting liposomes can be cross-linked for stabilization by polymerization initiators in the same manner as for the non-charged liposomes described above.

Thus, in one embodiment, the present invention encompasses polymerized liposomes which comprise (a) one or more of the fatty acids described above which may optionally be substituted with a suitable polymer spacer, activated linker, and one or more lectin targeting molecules; (b) one or more of the negatively charged polymerizable lipids described herein; (c) one or more non-polymerizable fatty acids or phospholipids; and (d) optionally cholesterol. Preferably, the polymerized liposomes comprises from about 0% to about 15% fatty acid and about 0% to about 100% negatively charged polymerizable lipids; and about 0% to about 50% non-polymerizable fatty acids, phospholipids or cholesterol; for example, DODPC/DODPG/Targeted fatty acid/cholesterol/DSPC.

4.5. Formulations/Compositions

The polymerized liposomes and targeted polymerized liposomes of the present invention are used as the carriers in a drug delivery system, especially an oral drug delivery system. The present invention thus also encompasses therapeutic formulations and compositions using these polymerized liposomes. The following describes representative materials which can be encapsulated in the liposomes of the present invention to form therapeutic compositions, methods of encapsulating those materials, and modes of administering the therapeutic compositions to a patient.

4.5.1. Materials to be Encapsulated

The polymerized liposomes of the present invention have utility for the oral and/or mucosal delivery of vaccines, antigens, allergens, diagnostic agents therapeutic agents and drugs. The polymerized liposomes of the present invention may be designed to carry a wide variety of antigens including, but not limited to diphtheria toxoid, influenza hemeagglutinin, ospA antigen from Lyme disease bacterium, and HTLV envelope protein antigen. Antigens to poliovirus, rhinovirus, rabies, vaccinia, Epstein-Barr virus, hepatitis, HTLV, herpes virus and human immunodeficiency virus are just examples of the many types of antigens which may be encapsulated into the liposomes of the present invention.

The polymerized liposomes of the present invention can be used for the oral and/or mucosal delivery of a wide variety of therapeutics, including but not limited to, antineoplastic agents, antibiotics, antifungals, antimicrobials, vaccines, insulin, cytokines, interferon, hormones, calcitonin, fertility drugs, antiviral agents (ddi, AZT, ddc, acyclovir and the like), antibacterial agents, DNA and RNA nucleotides, i.e., useful for gene therapy.

As used herein, the term "biologically active substance" refers to eukaryotic and procaryotic cells, viruses, vectors, proteins, peptides, nucleic acids, polysaccharides and carbohydrates, lipids, glycoproteins, and combinations thereof, and synthetic organic and inorganic drugs exerting a biological effect when administered to an animal. For ease of reference, the term is also used to include detectable compounds such as radiopaque compounds including air and barium, magnetic compounds, fluorescent compounds, and radioactive compounds. The active substance can be soluble or insoluble water. Examples of biologically active substances include anti-angiogenesis factors, antibodies, antigens, growth factors, hormones, enzymes, and drugs such as steroids, anti-cancer drugs or antibiotics, as well as materials for use as insecticides or insect repellents, fertilizers and vitamins, or any other material having a biological effect where controlled release is desirable.

In a diagnostic embodiment, the polymerized liposome incorporates a pharmaceutically acceptable gamma-emitting moiety, including but not limited to, indium and technetium, magnetic particles, radiopaque materials such as air or barium and fluorescent compounds.

4.5.2. Encapsulation of Biologically Active Material

Materials are generally incorporated into the liposomes at the time of formation, following polymerization using sonication of a solution of the material which contains the liposomes, and following polymerization by rehydration of a thin film of the liposomes.

The following is a general method for the preparation of polymerized liposomes wherein a biologically active substance is entrapped prior to the polymerization of the monomeric polymerizable liposome. First, the monomeric liposome can be prepared by the thin film hydration of polymerizable phospholipids and fatty acid mixture as described above. To form the thin film, a monomeric phospholipid and, optionally, a polymerizable fatty acid or targeted polymerizable fatty acid, is dissolved, in a suitable organic solvent such as chloroform, and the solution is then dried to form a thin film of phospholipid. Alternatively, a mixture of polymerizable phospholipid, fatty acids and targeting reagents is dissolved in tertiary butanol. The mixture is lyophilized to create a powdery substance that can be easily rehydrated for liposome generation and entrapment of payload drug or protein. A solution containing substance to be entrapped is added. At this stage, it is preferable to establish an inert atmosphere. The lipid film is then hydrated by gently shaking and sonicating the solution at a temperature of from about 30 to 50° C., usually around 40° C., for between five minutes and two hours, preferably around five minutes. Once the lipid film is hydrated, the trap ratio of the liposome can be increased by performing one or more freeze-thaw cycles on the liposome solution. This is particularly useful when the material being incorporated is hydrophilic in nature. Next, the polymerization is initiated in the presence of free radical initiators such as sodium bisulfite and potassium persulfate at a temperature between 25° C. and 40° C. until the polymerization is essentially complete. The desired degree of polymerization is from 30 to 100 percent.

Unentrapped biologically active substance can be removed by several means, including repeated centrifugation, decantation, gel filtration, and dialysis. The polymerized liposomes are then suspended in a buffer solution. The buffer solution has a pH preferably between pH 4.5 and pH 9.5, more preferably at physiological pH.

This method of entrapping biologically active substances is preferred because it does not involve the use of organic solvents. Use of organic solvents can denature biologically active substances. Further, the temperature requirements are mild, with the temperature typically not exceeding 40° C.

Materials can be entrapped within the liposomes, as well as or alternatively in one or more of the lipid layers of the phospholipid bilayer. This is typically determined by the hydrophobicity/hydrophilicity of the material to be incorporated as well as the method of preparation.

4.5.3. Modes of Administering the Polymerized Liposomes to a Patient

The polymerized liposomes of the present invention are administered by those routes which optimize uptake by mucosa. For example, oral, sublingual, buccal, rectal, vaginal and intranasal are preferred routes of administration. However, topical, transdermal and parenteral delivery may also be used. The most preferred route is oral. Further, the polymerized liposomes are particularly suitable for delivery through mucosal tissue or epithelia. The polymerized liposomes of the invention can be delivered orally in the form of tablets, capsules, cachets, gelcaps, solutions, suspensions, creams, ointments, suppositories and the like. When the dosage unit form is a capsule, it can contain, in addition to the material of the above type, a liquid carrier or adjuvant, when the liposomes contain an antigen. If administered topically the liposomes will typically be administered in the form of an ointment or transdermal patch. If administered intranasally the liposomes will typically be administered in an aerosol form, spray, mist or in the form of drops. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

The polymerized liposomes of the present invention are suitable for administration to mammals, including humans, as well as other animals and birds. For example, domestic animals such as dogs and cats, as well as domesticated herds, cattle, sheep, pigs and the like may be treated or vaccinated with the polymerized liposomes of the present invention.

The polymerized liposomes of the present invention have use in vaccine preparations. The preparation of vaccines containing an immunogenic polypeptide as the active ingredient is known to one of skill in the art.

4.5.4. Vaccine Formulations

Suitable preparations of vaccines include liquid solutions or suspensions; solid forms such as capsules and tablets, liquids for injections, may also be prepared. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Examples of adjuvants which may be effective, include, but are not limited to: aluminum hydroxide, muramyl dipeptides, including N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, saponins, saponin derivatives and fractions, QuilA, polymer adjuvants, including but not limited to block copolymers of polyethylene oxide and polypropylene oxide, monophosphoryl lipid A, lipid A derivatives, cholera toxin or *E. Coli* heat labile toxin, non-toxic mutants of cholera toxin or labile toxin.

The effectiveness of an adjuvant may be determined by measuring the induction of antibodies or cellular immunity directed against an immunogenic polypeptide containing an antigenic epitope, the antibodies resulting from administration of this polypeptide in vaccines which are also comprised of the various adjuvants.

The polypeptides may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium, potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal, rectal, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

The vaccine formulations of the invention comprise an effective immunizing amount of the antigenic protein and a pharmaceutically acceptable carrier or excipient. Vaccine preparations comprise an effective immunizing amount of one or more antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulations can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water-free concentrate in a hermetically sealed container such as an ampoule or sachet indicating the quantity of active agent. Where the composition is administered by injection, an ampoule of sterile diluent can be provided so that the ingredients may be mixed prior to administration.

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

Use of purified antigens as vaccine preparations can be carried out by standard methods. For example, the purified protein(s) should be adjusted to an appropriate concentration, formulated with any suitable vaccine adjuvant and encapsulated within the polymerized liposome. Suitable adjuvants may include, but are not limited to: mineral gels, e.g., aluminum hydroxide; surface active substances such as lysolecithin or pluronic polyols; polyanions; peptides; oil emulsions; alum, and MDP. The immunogen may also be incorporated into liposomes, or conjugated to polysaccharides and/or other polymers for use in a vaccine formulation. In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Effective doses (immunizing amounts) of the vaccines of the invention may also be extrapolated from dose-response curves derived from animal model test systems.

The present invention thus provides a method of immunizing an animal, or treating or preventing various diseases or disorders in an animal, comprising administering to the animal an effective immunizing dose of a vaccine encapsulated within a polymerized liposomes of the present invention.

Certain embodiments of the invention are illustrated, and not limited, by the following working examples.

5. EXAMPLE 1

(A) Synthesis of 2,4-ODPEG 2,4-ODPEG was synthesized as follows. 50 mg of 2,4-octadecadienoic acid (2,4-OD) was dissolved in 5 ml of N,N-dimethylformamide (DMF) under inert gas (argon), with constant stirring. 1.78 g of polyethylene glycol (average molecular weight of 400) and 217 mg of dimethylaminopyridine (DMAP) were added. Then 410 mg of 1-ethyl-3-(3-dimethylaminopropyl)carbodiimide HCl (EDCI) was added, and the solution stirred at room temperature for 24 hours. The reagent vessel was kept wrapped in aluminum foil during this time, to protect against UV degradation. The reaction was then quenched by the addition of a few milliliters of ice water, to destroy remaining EDCI. DMF and water were then evaporated under vacuum.

The compound thus obtained was purified in two stages. First, it was purified by dialysis against distilled water (500 ml) in a Spectraphor® dialysis tube (MWCO 500). The dialysis procedure was repeated a total of four times. The solution was evaporated under vacuum and then further purified by reversed-phase chromatography. The column (RP18) was first washed with water, then the fraction containing ODPEG was eluted using a 4:1 ethanol:water eluent. The fraction collected was evaporated under vacuum, to give a 53% yield of 2,4-ODPEG. The 2,4-ODPEG product was analyzed by thin layer chromatography (TLC) and by ultraviolet (UV) absorption spectroscopy ($\lambda_{max}$=255 nm).

(B) Synthesis of 2,4-ODPEG 110 mg of 2,4-octadecadienoic acid (2,4-OD) (NOF Corp., Japan), 61 mg of dimethylaminopyridine (DMAP, Aldrich) and 0.84 g of polyethylene glycol (Averg. M.W. 400, Aldrich) were dissolved in 7 ml of distilled methylene chloride under argon gas with constant stirring. Then, 72 mg of 1-ethyl-3-(3-dimethylaminopropyl)carbodiimide Hcl (EDCl) (Aldrich) was added (cooling if necessary), and the solution was stirred at room temperature for 24 hours. The reagent vessel was kept wrapped in aluminum foil during this time. The reaction was then quenched by the addition of a few milliliters of water. The organic solvent was removed under reduced pressure.

The compound thus obtained was purified in two stages. First, it was purified by dialysis against distilled water (500 ml×4) in a Spectra/Por dialysis tube (MWCO 500). The inner solution was lyophilized and the resulting white solid was further purified by reversed-phase column chromatography. The column (RP-18, EM Science) was eluted with water followed by a 4:1 ethanol:water eluent. The fraction collected was concentrated then lyophilized to give 207 mg (80% yield) of a hygroscopic white solid product with $\lambda_{max}$=266 nm.

(C) Synthesis of 2,4-ODPEGSu

The 2,4-ODPEG succinic acid derivative (2,4-ODPEGSu) was then prepared by reacting 2,4-ODPEG with succinic anhydride. First, 41 mg of 2,4-ODPEG and 25 mg of succinic anhydride (Aldrich) were dissolved in 2 ml of methylene chloride. 8.3 mg of DMAP was added, and the reaction was stirred at room temperature, under nitrogen gas protection and with the vessel tightly sealed and wrapped in aluminum foil, for 24 hours. The reaction was quenched by addition of a few milliliters of ice water, then evaporated to dryness under vacuum. The resulting product was purified first by dialysis and reversed phase chromatography, as described above, then by a second dialysis stage (MWCO 1000). The product was freeze-dried, and kept at −20° C. The yield of 2,4-ODPEGSu obtained from 2,4-ODPEG in this example was quantitative, so that the total synthesis of the polymerizable fatty acid has a yield, in this example, of about 53%.

6. EXAMPLE 2

Coupling of 2,4-ODPEGSu with EEA

A polymerizable fatty acid was coupled to a lectin, and the degree of lectin modification determined, according to the following method.

6.1. Materials and Methods

Coupling of 2,4-ODPEGSu with EEA

EEA was coupled to 2,4-ODPEGSu by the following method. 0.5 mg of 2,4-ODPEGSu was dissolved in 0.6 ml of a pH 5.4 MES buffer (2-(N-morpholino)ethane-sulfonic acid, sodium salt) (Aldrich). 3 mg of N-octylglucoside, 5 mg of EDCI, and 11.5 mg of N-hydroxylsulfosuccinimide (NHS) were added. The reaction was run at room temperature for 5 minutes, with constant stirring. Next, 1.46 mg of EEA in a phosphate buffered saline (PBS) solution, and 0.5 ml of 1 molar HEPES buffer were added. The pH of the solution was adjusted to 7.6, and the solution was stirred at 4° C. overnight. The product was dialyzed against 0.2 mM PBS (300 ml×5) in a Spectra Por dialysis tube (MWCO=2, 000) for a total of 30 hours. The purified product was transferred to a vial and kept at 4° C. until further use. Other lectins can be linked to 2,4-ODPEGSu by following a similar procedure.

Determination of the Degree of Lectin Modification

The degree of lectin modification is determined as follows. Five stock solutions are prepared:

Solution A: 0.1M $Na_2B_4O_7$ in 0.1M NaOH

Solution B: 0.1M $NaH_2PO_4$

Solution C: 0.1M $Na_2SO_3$ (prepared within 48 hours)

Solution D: 10 ml of Solution B+0.15 ml of Solution C

Solution E: 50 ml of TNBS in 5 ml distilled water where TNBS is 2,4,6-trinitro-benzenesulphonic acid (SIGMA). 0.685 ml of the 2,4-ODPEGSu-EEA solution (protein concentration of 0.292 mg/ml) is diluted with solution A to a final volume of 1 ml. To this is added 100 µl of solution E and mixed vigorously. The resulting solution is incubated at 40° C. for 45 minutes, then the reaction is stopped by addition of 1 ml of solution D. A standard solution is prepared by mixing 100 µl of solution E in 1 ml of solution A and 1 ml of solution D. The degree of lectin modification is then calculated from the absorbance of the solution at 420 nm. The degree of modification in this example is 51%.

7. EXAMPLE 3

Polymerizable Liposomes Incorporating Membrane Proteins

DODPC is dissolved in octylglucoside, and the desired peptide is dissolved in PBS. The peptide solution is then added to the lipid inside of a dialysis membrane (MWCO= 10,000) and dialyzed versus PBS (2 ml versus 1 liter) for approximately four hours, with two changes of PBS. The liposomes spontaneously form in the dialysis membrane. The liposomes thus formed can be polymerized using a redox couple initiator (e.g., $NaHSO_3$ and $K_2S_2O_8$).

8. EXAMPLE 4

Polymerized Liposomes

A mixture of lipids containing a polymerizable lipid can be lyophilized to form a powdery material, then rehydrated with a solution containing the desired peptides or antigens to be encapsulated in the liposome or to be incorporated into the lipid bilayer. The rehydrating takes place at a temperature above the melting point of the lipid mixture. The resulting liposomes are then sonicated at 45° C. for approximately 5 minutes to reduce the size of the liposomes to around the 200 nm range. The liposomes are then polymerized using any known technique. The free peptide can be separated from the liposomes by centrifuging the liposomal preparation at approximately 100,000×g. Alternatively, the polymerized liposome solutions can be passed through an ultrafiltration column to purify and concentrate the liposomes containing peptide.

A preferred method uses a mixture of 2,4-DODPC and lectin-modified 2,4-ODPEGSu as the polymerizable lipid mixture, dissolved in tert-butanol. After rehydration with a solution of the desired peptide or antigen, the liposomes are sonicated and polymerized using a sodium bisulfite (580 $\mu$M) potassium persulfate (127 $\mu$M) redox couple initiator.

9. EXAMPLE 5

Measurement of the Absorption of Biologically Active Substances Entrapped in Polymerized Liposomes Polymerized liposomes containing $^{125}$I-BSA can be orally administered to rats. The absorption of $^{125}$I-BSA into the blood can then be examined. $^{125}$I-BSA containing monomeric liposomes and $^{125}$I-BSA solution are used as controls. The polymerized liposomes are prepared as described infra.

Each formulation, including the control $^{125}$I-BSA solution, is administered intragastrically with a ball-tipped needle and blood is sampled at appropriate intervals from the tail vein. To distinguish between transport of $^{125}$I-BSA in the context of liposomes, free $^{125}$I-BSA and the radiolabelled degradation product of $^{125}$I-BSA, the blood samples are separated into three fractions: 1) cell debris fraction, 2) trichloroacetic acid (TCA) precipitable fraction, and 3) TCA non-precipitable fraction.

Feces of rats are homogenized with water and centrifuged to separate solids. Radioactivity in the whole homogenate and sedimented solid are then compared. In the case of polymerized liposome administered rats, the difference in the amount of total radioactivity observed in the solid, compared with the amount from monomeric liposome administered rats, shows the relative stability of polymerized liposomes in the G-I tract.

Because elimination of the precipitable fraction in blood after intravenous injection can be slow, the TCA non-precipitable fraction is smaller in animals administered material in polymerized liposomes, as compared to material administered in conventional liposomes and significantly less than when material is administered in solution.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A polymerizable fatty acid of the formula:

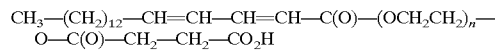

wherein n is an average number of —OCH$_2$CH$_2$— units from about 4 to about 45, or a pharmaceutically acceptable salt thereof.

2. The fatty acid of claim 1 wherein n is an average number of —OCH$_2$CH$_2$— units from about 6 to about 12.

3. A polymerizable fatty acid according to claim 1 which further comprises a targeting ligand covalently bound to said polymerizable fatty acid.

4. The polymerizable fatty acid of claim 3 wherein said targeting ligand is a lectin.

5. The polymerizable fatty acid of claim 4 wherein said lectin is UEA, WGA, EEA or FITC-EEA.

* * * * *